United States Patent [19]

Barson et al.

[11] Patent Number: 4,540,398
[45] Date of Patent: Sep. 10, 1985

[54] KNITTED SURGICAL SWABS

[75] Inventors: Craig Barson, Skipton, England; Thomas Denny, East Brunswick, N.J.

[73] Assignee: Johnson & Johnson Products, Inc., New Brunswick, N.J.

[21] Appl. No.: 510,110

[22] Filed: Jul. 1, 1983

[30] Foreign Application Priority Data

Mar. 29, 1983 [GB] United Kingdom ............... 8308674

[51] Int. Cl.$^3$ .............................................. A61F 13/00
[52] U.S. Cl. ....................................... 604/1; 604/362; 604/384; 66/195
[58] Field of Search ..................... 604/1, 90, 358, 384, 604/362; 128/334; 66/169 R, 170, 192, 195, 193, 196

[56] References Cited

U.S. PATENT DOCUMENTS

| 3,124,136 | 3/1964 | Usher | 128/334 R |
| 3,150,693 | 9/1964 | Seltzer | 604/384 X |
| 4,347,847 | 9/1982 | Usher | 128/334 R |

FOREIGN PATENT DOCUMENTS 1293166 10/1972 United Kingdom .
1478454 6/1977 United Kingdom .

Primary Examiner—William H. Grieb
Attorney, Agent, or Firm—Wayne R. Eberhardt

[57] ABSTRACT

A surgical swab comprises a warp knitted body portion (1) and an integrally warp knitted handling tape (3). Both the body portion and the handling tape are formed as two superimposed layers on a twin needle bed knitting machine, the respective longitudinal and/or laterally extending edges of each layer being joined by interknitting.

The swab may be cut from a continuous swab strip which is formed by continuously knitting a length of body portion fabric and of handling tape fabric with a lateral band of the fabrics being knitted together at intervals. Individual swabs are separated from the strip by cutting through the lateral band.

7 Claims, 2 Drawing Figures

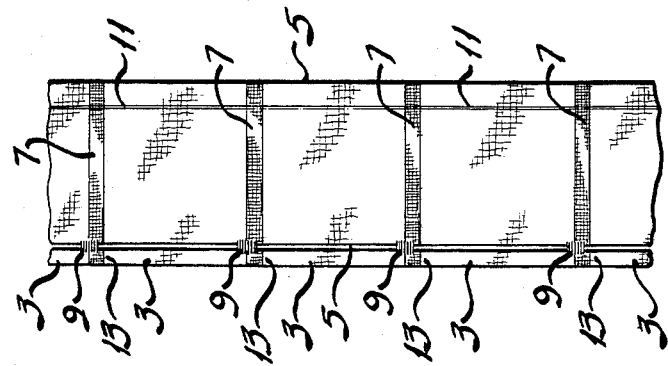
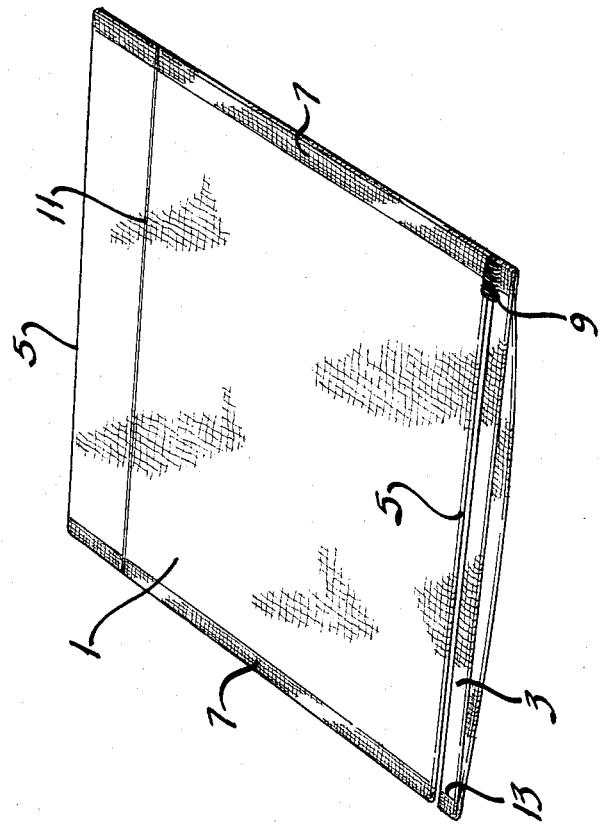

KNITTED SURGICAL SWABS

BACKGROUND OF THE INVENTION

This invention relates to surgical swabs, and to a process for producing such swabs.

Swabs used in surgical procedures are usually of three types, namely those used for skin preparation, those used for absorbing body fluids during a surgical operation, and those used for packing the body cavity while surgical work is carried out on the viscera. For each of these purposes, a surgical swab should have wettability, flexibility, softness of handle and a degree of resilience, particularly when wet. Swabs which are to be used within the body cavity should also be provided with means for locating the swab, since such swabs can otherwise be difficult to identify when saturated with blood or other body fluids.

Surgical swabs are conventionally manufactured by sewing together sufficient layers of a woven light surgical gauze or muslin to achieve the required thickness. The use of a large number of plies of a lighter woven fabric is preferred to the use of fewer plies of heavier woven cloths. Heavy woven cloths normally lack flexibility, and have relatively low absorbency because of the lack of interlayer capillaries.

Conventional surgical swabs are usually provided with a handling tape for locating the swab, such handling tapes usually being formed from a length of woven cotton fabric.

British Patent Specification No. 1478454 discloses a surgical swab which is cut from a length of warp or weft knitted fabric. The or each cut edge of the swab is enclosed within a folded tape, the tape being folded over the cut edge with the side edges of the tape tucked in and the tape secured to the cut edge of the swab. The purpose of this arrangement is to obviate possible fiber loss from the cut ends of the swab and from the side edges of the tape. Fiber loss is, of course, highly undesirable because discarded fibers may be retained in the body cavity of a patient, with consequent adverse effects.

The above-mentioned Specification also discloses that one of the edge tapes applied to the swab may extend beyond the width of the swab to act as a handling tape for locating the swab during surgical operations.

The swabs disclosed in Specification No. 1478454 have certain advantages over the conventional muslin swabs. A knitted structure differs from a woven fabric in that it consists of threads interlaced by looping. This looped structure tends to make knitted fabrics more flexible, more deformable and thus apparently much softer to handle than a woven material of equivalent weight. Both warp and weft knitted structures can be produced which have the resilience, wettability and absorbency of a multiplicity of layers of conventional woven fabrics.

Despite these advantages the surgical swabs of Specification No. 1478454 has not received the anticipated commercial acceptance, most probably because of the relatively high cost of the manual operations involved in converting the knitted fabric into swabs.

SUMMARY OF THE INVENTION

We have now devised a surgical swab which has the advantages of a knitted structure, while avoiding the need for elaborate and hence relatively costly manual operations.

According to the present invention there is provided a surgical swab comprising a warp knitted body portion, and an integrally warp knitted handling tape. Such a swab lends itself particularly well to economical continuous manufacture.

According to a further aspect of the present invention, there is provided a process for producing surgical swabs, comprising knitting a surgical swab strip by the alternate steps of (i) simulataneously warp knitting a predetermined length of body portion fabric and of handling tape fabric and (ii) knitting the body portion fabric and the handling tape together for a second predetermined length to effect a join between them, and subsequently cutting the surgical swab strip into individual surgical swabs having a handling tape with a free end.

DETAILED DESCRIPTION

The knitted surgical swabs of the present invention may be economically manufactured by a continuous knitting process wherein the body of the swab and the handling tape are knitted simultaneously and longitudinally adjacent swabs are connected by an interknitted band. The individual swabs are separated from the continuous knitted structure by simply cutting through each interknitted interconnecting band. Fibre loss from the cut ends of the warp knitted swabs is minimal, because the yarns of a warp knitted fabric, unlike those of a woven fabric, are retained in the structure by being looped around adjacent yarns.

The handling tape may be knitted to the body portion fabric using additional joining guide bars, the yarns for the joining fabric being laid into the body portion fabric or the handling tape fabric until required to effect the join. The joining fabric may, for example, be of 2 to 4 needle spaces in width.

Preferably, the body portion comprises two superimposed layers of fabric which are preferably interknitted at the longitudinal edges of the body portion, by which is meant the edges extending in the machine direction. Such a construction may be achieved on a double needle bed warp knitting machine, such as are already known for knitting tubular fabrics. The interknitting of side edges to effect a join between the two superimposed layers of fabric may be accomplished by the looping of warp yarns from one needle bed around the warp yarns of the second needle bed. Alternatively, the interknitting may be effected by the alternate looping of a warp yarn from one needle bed around a warp yarn of the second needle bed and the looping of a warp yarn from the second needle bed around a warp yarn of the first needle bed. Such procedures are described, for example, in British Patent Specification No. 1293166.

When the swab of the present invention has a body portion comprising two superimposed layers of knitted fabric, these layers may also be interknitted at their laterally extending edges, by which is meant the edges extending cross-wise to the machine direction.

Swabs comprising two superimposed layers of knitted fabric have considerably improved handling properties as compared with swabs comprising just a single layer of knitted fabric, for the reasons described above in relation to swabs of woven fabric.

The integrally-knitted handling tape may itself be of a single or of double layer construction, optionally having interknitted longitudinal and/or laterally extending edges. Preferably, the handling tape is a double layer construction interknitted only on the lateral edges to provide a loop construction which is preferred by surgeons.

It is particularly preferred that the cuts in the swab strip be made at points which are slightly displaced longitudinally relative to the join between the handling tape fabric and the body portion. This has the advantage that each cut yields a swab with a handling tape which is free at one end, and integrally knitted to the body portion adjacent the other end.

Preferred yarns for the swab of the present invention are those of an essentially hydrophilic nature, e.g., cotton, viscose rayon, or other regenerated celluloses or blends of these with synthetic fibers, e.g., polyester, nylon and polypropylene. Such yarns may, if desired, be scoured and bleached prior to the knitting operation, but it is greatly preferred that such scouring and bleaching be carried out after knitting the swab strip and before cutting it into individual swabs.

In order to facilitate detection in the body cavity, the surgical swabs of the present invention preferably has a detectable member incorporated therein. For example, an X-ray detectable marker may be incorporated into the swab. An example of such a marker is RAY-TEC X-ray detectable ribbon which may be inlaid or knitted into the fabric of the swab. Preferably, however, a barium sulphate loaded viscose thread is inlaid or woven into the fabric, since such a viscose thread possesses the higher strength which is desirable in a knitting process. Alternatively, for example, an electromagnetically detectable device may be incorporated in the swab.

Swabs according to the present invention may be supplied in bulk to hospitals for sterilization by steam or may be supplied pre-sterilized. Such pre-sterilization may, for example, be by steam, ethylene oxide, or gamma-irradiation at 25 kGy. The sterile swab may be contained in a hermetically-sealed sterile enclosure.

A swab according to the present invention, and a process for making the same, are now described by way of example, with reference to the accompanying drawings, in which:

FIG. 1 is an isometric view of a swab according to the invention, and

FIG. 2 is a plan view of a swab strip prior to cutting into individual swabs.

Referring to the drawings, a surgical swab comprises a warp knitted body portion 1, and an integrally warp knitted handling tape 3. The body portion 1 is knitted as a double layer of fabric each of approximately 120 g/m$^2$, on a double needle bed warp knitting machine having 18 needles per inch (2.54 cm). The two layers are interknitted at the longitudinal edges 5 and at the laterally extending edge regions 7 of the swab, so that the body portion forms, in effect, a fully enclosed pouch.

Similarly, the handling tape 3 is formed as a double layer which is interknitted at its laterally extending edges, and, in the illustrated embodiment, not interknitted at its longitudinal extending edges so as to form an open loop between the lateral extending edges.

The body portion 1 and the handling tape 3 are connected by a joining region 9. The yarns from which the joining region is formed are laid into the fabric of the body portion 1 for the entire longitudinal extent of the swab, except for the joining region itself.

An X-ray detectable thread 11 is also laid into the fabric of the body portion 1.

The swab of FIG. 1 is formed as a continuous swab strip (FIG. 2). Since the joining regions 9 are slightly displaced longitudinally relative to the interknitted laterally extending edge regions 7, a cut along the centre of each interknitted laterally extending edge region yields a swab having a handling tape which is free at one end 13, and integrally knitted to the swab fabric adjacent the other end.

We claim:

1. A surgical swab comprising a warp knitted body portion and an integrally warp knitted handling tape, said body portion being joined to said handling tape by means of a joining region consisting of yarns which are knitted into the fabric of the body portion and the handling tape where required to effect said join.

2. A surgical swab according to claim 1 having an X-ray detectable marker incorporated therein.

3. A surgical swab according to claim 1 contained in a sterile enclosure.

4. A surgical swab comprising a warp knitted body portion and an integrally warp knitted handling tape wherein the handling tape comprises two superimposed layers of warp knitted fabric, said two layers being joined by interknitting along their respective laterally extending edges while remaining non-joined along their respective longitudinally edges.

5. A surgical swab having a longitudinal machine direction and a transverse lateral direction, and comprising (i) a body portion constructed of two superimposed layers of warp knitted fabric interknitted along their respective longitudinal and laterally extending edges, and (ii) a longitudinally adjacent handling tape constructed of two superimposed layers of warp knitted fabric interknitted along their respective laterally extending edges, said handling tape and said body portion being joined by an interknitted segment of their respective adjacent longitudinal edges at one end thereof.

6. A surgical swab according to claim 5 having an X-ray detectable marker incorporated therein.

7. A surgical swab according to claim 5 contained in a sterile enclosure.

* * * * *